US 11,166,831 B2

(12) United States Patent
Myint

(10) Patent No.: US 11,166,831 B2
(45) Date of Patent: Nov. 9, 2021

(54) APPARATUS FOR PRODUCING STRIPS OF BONE FIBRE, AND A METHOD OF USING SUCH APPARATUS

(71) Applicant: Veterinary Tissue Bank Ltd., Chirk (GB)

(72) Inventor: Peter Myint, Chirk (GB)

(73) Assignee: Veterinary Tissue Bank Ltd, Chirk (GB)

( * ) Notice: Subject to any disclaimer, the term of this patent is extended or adjusted under 35 U.S.C. 154(b) by 121 days.

(21) Appl. No.: 16/086,308

(22) PCT Filed: Jul. 2, 2018

(86) PCT No.: PCT/GB2018/051853
§ 371 (c)(1),
(2) Date: Sep. 18, 2018

(87) PCT Pub. No.: WO2019/012248
PCT Pub. Date: Jan. 17, 2019

(65) Prior Publication Data
US 2021/0106438 A1    Apr. 15, 2021

(30) Foreign Application Priority Data
Jul. 11, 2017    (GB) ..................................... 1711130

(51) Int. Cl.
*A61F 2/46*    (2006.01)
*A61F 2/28*    (2006.01)
(Continued)

(52) U.S. Cl.
CPC ........ *A61F 2/4644* (2013.01); *A61B 17/1635* (2013.01); *A61F 2/3094* (2013.01);
(Continued)

(58) Field of Classification Search
CPC . A61F 2/28; A61F 2/4644; A61F 5/00; A61B 17/16; A61B 17/1635
See application file for complete search history.

(56) References Cited

U.S. PATENT DOCUMENTS

| 6,676,662 B1 | 1/2004 | Bagga et al. |
| 2004/0059364 A1 | 3/2004 | Gaskins et al. |

(Continued)

FOREIGN PATENT DOCUMENTS

| EP | 0 104 732 | 4/1984 |
| JP | 2002-306500 | 10/2002 |
| KR | 2014-0037908 | 3/2014 |

*Primary Examiner* — Jason-Dennis N Stewart
(74) *Attorney, Agent, or Firm* — Levy & Grandinetti

(57) ABSTRACT

Apparatus for producing strips of bone fibre comprising a vice for securing a section of rigid bone with which said apparatus is used, said vice defining a containment area and having a compression axis with which a longitudinal axis of said bone is substantially aligned in use, an arm for reciprocal linear movement along a movement axis between a rearward position and a forward position, said movement axis being parallel with said compression axis and spaced therefrom in a lateral plane, a first drive mechanism for moving said arm along said movement axis in a reciprocal manner, and a cutting head comprising a first row of cutting teeth, which cutting head is mounted to a first end of said arm with said first row of cutting teeth coincident with said containment area and disecting said lateral plane, and a method of producing a DBM fibres product using such apparatus.

31 Claims, 5 Drawing Sheets

(51) Int. Cl.
  *A61B 17/16* (2006.01)
  *A61F 2/30* (2006.01)
  *A61L 27/36* (2006.01)

(52) U.S. Cl.
  CPC ......... *A61L 27/365* (2013.01); *A61L 27/3608* (2013.01); *A61L 2430/02* (2013.01); *A61L 2430/40* (2013.01)

(56) References Cited

U.S. PATENT DOCUMENTS

| | | |
|---|---|---|
| 2007/0164137 A1 | 7/2007 | Rasekhi |
| 2014/0314822 A1 | 10/2014 | Carter et al. |
| 2016/0206781 A1 | 7/2016 | Kakabadze et al. |
| 2017/0181755 A1 | 6/2017 | Librot |

APPARATUS FOR PRODUCING STRIPS OF BONE FIBRE, AND A METHOD OF USING SUCH APPARATUS

The present invention relates to apparatus for producing strips of bone fiber, and a method of using such apparatus, for use particularly, but not exclusively, to produce demineralised bone matrix (DBM) fibres for use in orthopaedic procedures.

DBM is used in various orthopaedic procedures are dental/maxillofacial reconstructive surgery where accelerated fusion of bone is desired. Unlike conventional bone grafting materials which act as an osteoconductive scaffold to fill the bone defects. DBM contains growth factors such as bone morphogenic proteins (BMPs) to induce new bone formation, and as such is both osteoconductive and osteoinductive.

DBM is formed from cortical bone, and is usually taken from the femur or tibia. Traditionally the bone is commonly milled into small particles in the range of over 100 um to around 1 mm, and is then subjected to a demineralisation process by being soaked in a mild acid solution, normally 0.5 M or 0.6 M hydrochloric acid, for a few hours. The demineralisation process removes minerals, mainly calcium, from the bone. This allow the growth factors which reside in the remaining collagen matrix of the bone to express their biological function when implanted into the body. DBM products are prepared either in the form of particles, or they are mixed with gelling agents to form a mouldable putty.

Alternatively, DBM can be made from strips of bone fibre rather than particles. Bone fibre strips are believed to provide improved bone healing properties because they are elongate and mesh together, which allows host cells to migrate into the implanted graft instead of having to jump from one particle to another, in addition, bone fibre strips also provide a larger surface area for cell attachment, which also improves the bone healing process. They also tend to stay in situ in the bone defect compared to the particles which can easily to be washed away by the body fluid.

However, cortical bone is a very hard calcified tissue, and it is brittle in nature due to the microstructure of collagen fibres and the calcium phosphate compound deposited thereon. Cutting or shaving cortical bone into long thin trips often results in the breaking up or crumbling of the strips. In addition, maintaining the continuous elongate shape of the bone strips after they have been soaked in acid solution and subsequently dried poses additional challenges. As such, a suitable method and equipment to make such bone fibre strips on an industrial scaled has not materialised, and DBM particles remain the main source for preparation of DBM products. To date, only a very limited number of DBM acts made using bone fibre strips are available on the market.

The present invention is intended to overcome some of the above described problems.

Therefore, according to a first aspect of the present invention apparatus for producing strips of bone fibre comprises a vice for securing a section of rigid bone with which said apparatus is used, said vice defining a containment area and having a compression axis with which a longitudinal axis of said bone is substantially aligned in use, an arm for reciprocal linear movement along a movement axis between a rearward position and a forward position, said movement axis being parallel with said compression axis and spaced therefrom in a lateral plane, a first drive mechanism for moving said arm along said movement axis in a reciprocal manner, and a cutting head comprising a first row of cutting teeth, which cutting head is mounted to a first end of said arm with said first row of cutting teeth coincident with said containment area and directing said lateral plane.

Thus, the present invention provides apparatus which employs a linear relative movement between the section of bone and the cutting head in order to shave strips of bone fibre therefrom as the cutting head moves from the rearward to the forward positon, or vice versa. Preferably the first row of cutting teeth are arranged to cut the bone as the arm moves from the rearward to the forward position.

Preferably the apparatus can comprise a first adjustment mechanism for adjusting the location of the cutting head in the lateral plane between an upper position and a lower position, Alternatively the apparatus can comprise a first adjustment mechanism for adjusting the location of the vice in the lateral plane between an upper position and a lower position. The relative movement between the cutting head and the vice is the same in each case, and that is what is relevant and allows for the thickness of the strips of bone fibre to be set. The first adjustment mechanism can be manually settable, for example with a rack and pinion, a rotating screw or similar. However, preferably the apparatus can comprise a second drive mechanism for driving the first adjustment mechanism, whether it moves the cutting head or the vice. As such, the thickness of the strips of bone fibre which are produced can be automatically established by the user. The first adjustment mechanism and the second drive mechanism can be any known mechanical apparatus which can achieve the above described movements, and many alternatives are known. For example, the first adjustment mechanism can be a rack and pinion, and the second drive mechanism can be an electrical motor which can rotate e pinion to move the cutting head or the vice linearly in the lateral plane. In preferred constructions the first adjustment mechanism can adjust the location of the cutting head or the vice in the lateral plane by increments of between substantially 0.1 mm and substantially 0.4 mm, such that the resulting strips of bone fibre comprise such thicknesses.

The first adjustment mechanism can adjust the location of the cutting head or the vice in the lateral plane between each reciprocal movement of the arm along the movement axis, such that the thickness of a continuous sequence of strips of bone fibre cut from the section of rigid bone are substantially consistant. It will be appreciated how this can be done automatically using something like an electrical motor to rotate a pinion of a rack and pinion arrangement in small increments each time the first drive mechanism moves the arm back the rearward position.

The apparatus can also comprise a second adjustment mechanism adjusting location of the cutting head in a transverse plane normal to the lateral plane between a left position and a right position. Alternatively the apparatus can comprise a second adjustment mechanism for adjusting the location of the vice in a transverse plane normal to said lateral plane between a left position and a right position. The relative movement between the cutting head and the vice is the same in each case, and that is what is relevant and allows the user to set the area of the section of rigid bone from which the strips of bone fibre are to be cut. The second adjustment mechanism can be manually settable, for example with a rack and pinion, a rotating screw or similar. However, preferably the apparatus can comprise a third drive mechanism for driving the second adjustment mechanism. As such, the area of the section of bone from which the strips are to be cut can be automatically set by the user. The second adjustment mechanism and the third drive mechanism can be any known mechanical apparatus which can achieve the above described movements, and many alternatives are known. For example, the second adjustment mechanism can be a rack and pinion, and the third drive mechanism can be an electrical motor which can rotate the pinion to move the cutting head or the vice linearly in the transverse plane.

The apparatus can also comprise a third adjustment mechanism for adjusting the location of the rearward position and the forward position of the arm on the movement axis. This allows the user to set the length of the strips of bone fibre which are cut. The third adjustment mechanism can be manually settable, but preferably the apparatus can comprise a fourth drive mechanism for driving the third adjustment mechanism. As such, the length of the strips of bone fibre which are cut can be automatically set by the user. The third adjustment mechanism and the fourth drive mechanism can be any known mechanical apparatus which can achieve the above described movements, and many alternatives are known. For example, if the first drive mechanism which moves the arm is a hydraulic ram or the like, then the third adjustment mechanism can be any means to control the degree of extension of the ram, for example a stop which acts on the piston inside the ram, and the fourth drive mechanism can be any means to adjust the position of the stop, such an electrically controlled rack and pinion or screw or the like. Alternatively, the third adjustment mechanism can be an adjustable linkage which adjusts the throw of a connecting rod forming a part of the first drive mechanism, and the fourth drive mechanism can be a piston, or an electrical motor, which acts on the connecting rod. In a preferred construction the third adjustment mechanism can adjust the location of the rearward position and the forward position of the arm on the movement axis so the relative spacing between them is between substantially 40 mm and 100 mm, such that the resulting strips of bone fibre comprise such lengths.

The first, second and third adjustment mechanisms, and the first, second, third and fourth drive mechanisms can be controlled by a microprocessor, which can comprise an operation key pad and screen, allowing the user to set the various parameters described above. Such systems are widely known and the skilled person will be able to implement the above described features by reference to their common general knowledge in the field. Therefore, such finer details of the apparatus of the invention are not described herein in greater depth.

The vice can be any known vice contraction which can secure a section of bone between opposing parts, which have the compression axis between them. The containment area referred to above is an area occupied by an e held by the vice, and as such is it not just the area between the opposing parts thereof. In this case the containment area is that occupied by the section of bone, which may be within the area between the opposing parts of the vice, or it may be beyond the area between the opposing parts. It is simply necessary that it is an area through which the cutting head can move back and forth.

The cutting head of the invention can be any shape or configuration comprising a row of cutting teeth. However, preferably the cutting head can comprise a lower end face with a plurality of parallel troughs formed therein, and the first row of cutting teeth can comprise remaining portions of a leading edge of the lower end face between the troughs. In other words the cutting head can have a crenelated shape in which the cutting teeth are at the top of each of the battlements thereof.

Preferably the plurality of parallel troughs extend from the leading edge to a trailing edge of the lower end face. Further, the lower end face can be at an angle of substantially 15 degrees to the compression axis, and the trailing edge can be spaced from the compression axis a greater distance than the leading edge. This construction allows the first row of cutting teeth to move cleanly over the bone without binding.

The apparatus can further comprise a second row of cutting teeth comprising leading edges of inner ends of the plurality of parallel troughs. As such, the second row of cutting teeth are formed by the bases of the battlements of the crenelated shape of the cutting head. With this formation the first row of cutting teeth initiate the cutting of the section of bone, and the second row of cutting teeth begin to cut the bone when the depth of the cuts formed by the first row or cutting teeth equal the depth of the troughs. From that point, both the first row of cutting teeth and the second row of cutting teeth will both cut strips of bone fibre from the section of bone. This construction allows for the maximum number of strips of bone fibre to be cut from the section of bone. The depth of the troughs is greater than the thickness of the strips of bone fibres cut from the section of bone in order to allow for the second row of teeth to come in contact with the section of bone.

The cutting head can comprise front face which is at an angle to the transverse plane referred to above, such that said second row of cutting teeth is rearward of said first row of cutting teeth. This shape occurs because the first row of cutting teeth need to be arranged at an angle to the section of bone in order to cut it. Preferably the first row of cutting teeth comprises a cutting angle of substantially 5 degrees to the transverse plane. The second row of cutting teeth can comprises the same cutting angle. With this arrangement the cutting teeth are applied to the surface of the section of bone at an angle of substantially 95 degrees (as the transverse plane is normal thereto). This angle has been chosen because it produces thin slilces of bone fibre while at the same time preventing the teeth from being chipped away by the force applied by the first drive mechanism.

The width of each tooth of the first row cutting teeth can be between substantially 1 mm and substantially 2 mm. As such, the width of the strips of bone fibre cut from the of bone will have the same width. It will be appreciated though that the first row of cutting teeth can comprise much larger widths in order to create sheets or straps of bone fibre if desired.

The cutting head can be any shape which can support the first row cutting teeth and which can be attached to the arm. However, in a preferred construction the apparatus can comprise a bone rake comprising an elongate stem with the cutting head formed at a first end thereof. The bone rake can be removably mountable in the first adjustment mechanism elongate stem aligned with the lateral plane. (It will be appreciated that in versions of the invention in which the cutting head is moved left and right in the transverse plane by the second adjustment mechanism, the elongate stem will move left and right of the lateral plane when the position of the cutting head is adjusted in that way, but the elongate stem is aligned with the lateral plane in a central position of the second adjustment mechanism. In versions of the invention in which the vice is moved left and right in the transverse plane by the second adjustment mechanism, the elongate stem is always aligned with the lateral plane.)

It will be appreciated that as the bone rake is removable, the apparatus carp comprise two or more such bone rakes, each with different widths of teeth thereof. This allows for the width of the strips of bone fibre cut from the section of bone to be adjusted by the user to suit. Further, it also allows for bone rakes with different widths of cutting head to be used, to accommodate different diameters of bone shafts being cut.

Therefore, according to a second aspect of the present invention, a kit of parts comprises apparatus for producing strips of bone fibre comprising a vice for securing a section of rigid bone with which said apparatus is used, said vice defining a containment area and having a compression axis with which a longitudinal axis of said bone is substantially aligned in use, an arm for reciprocal linear movement along a movement axis between a rearward position and a forward position, said movement axis being parallel with said compression axis and spaced therefrom in a lateral plane, a first drive mechanism for moving said arm along said movement axis in a reciprocal manner, and a first cutting head comprising a first row of cutting teeth, which first cutting head is removably mountable to a first end of said arm with said first row of cutting teeth coincident with said containment area and disecting said lateral plane; and, one or more further cutting heads each comprising a first row of cutting teeth with teeth of a different width to teeth of said first cutting head, each of which one or more further cutting heads is removably mountable to a first end of said arm with said first row of cutting teeth coincident with said containment area and disecting said lateral plane.

The invention also includes a method of producing strips of bone fibre using apparatus as described above.

Therefore, according to a third aspect of the present invention a method of producing a DBM fibres product using apparatus as claimed in any of claims 1 to 19 below, comprises the steps:

i) securing a section of rigid bone in a vice of said apparatus with a longitudinal axis thereof substantially aligned with a compression axis of said vice;

ii) operating a first drive mechanism of said apparatus to move an arm of said apparatus along a movement axis thereof in a reciprocal manner, such that a first row of cutting teeth of a cutting head of said apparatus cuts strips of bone fibre from said section of rigid bone; and iii) formulating a DBM fibres product comprising the cut strips of bone fibre.

One important aspect of this method is that the section of bone is rigid. This is necessary for the apparatus described above to operate. This is in contrast to some known methods of producing a DBM fibres product in which the section of bone is demineralised before it is cut to such an extent that it is no longer rigid. That is not the case with the method of the third aspect of the present invention, which involves cutting strips of bone fibre from substantially unprocessed and non demineralised sections of bone. As explained below, the demineralisation process is performed in a later step.

The method can include the additional step of operating a first adjustment mechanism of the apparatus to adjust the location of the cutting head or the vice in a lateral plane between an upper position and a lower position to set the thickness of strips of bone fibre cut from the section of rigid bone.

The method can include the additional step of operating e first adjustment mechanism to adjust the location of the cutting head or the vice in the lateral plane, between each reciprocal movement of the arm along the movement axis, such that the thickness of a continuous sequence of strips of bone fibre cut from the section of rigid bone are substantially consistant.

The method can include the additional step of operating second adjustment mechanism mechanism of the apparauts to adjust the location of the cutting head or the vice in a transverse plane between a left position and a right position, to set the area of the section of rigid bone from which the strips of bone fibre are cut.

The method can include the additional step of operating a third adjustment mechanism of the apparatus to adjust the location of a rearward position and a forward position of the arm on the movement axis to set the length of strips of bone fibre cut from the section of rigid bone.

The above described steps involve operating and adjusting the apparatus of the first aspect of the present invention in order to obtain strips of bone fibre, in a first stage of the method of the third aspect of the present invention. In a second stage those strips of bone fibre are further processed in the known ways to produce a DBM fibres product.

Therefore, the method can include the additional step of demineralising the cut strips of bone fibre by immersing them in hydrochloric acid of between 0.5 M to 0.6 M until the cut strips of bone fibre are within the range of between substantially 1% and substantially 4% w/w of residual calcium content.

The demineralised cut strips of bone fibre can then be neutralised in a buffer solution and washed thoroughly in water. They can then be freeze dried and used as bone grafting materials. However, alternatively the method can include the additional step of mixing the demineralised cut strips of bone fibre with one or more gelling liquids, chosen from glycerol, gelatin and/or cellulose to form a surgical mixture.

The demineralised cut strips of bone fibre can then be further processed by being digested in enzymes such as trypsin or some mild acids to make injectable bone gel without impairing the osteoinductive properties.

The method can include the additional step of pressforming the surgical mixture into a predetermined shape chosen from a ball, a boat, a pellets a cylinder or a cone.

Finally, the method can include the additional step of mixing the demineralised cut strips of bone fibre with one or more pharmaceutically active additives chosen from antibiotics, calcium phosphate based materials, stem cells and or growth factors.

According to a fourth aspect of the present invention there is provided DBM fibres product produced using the method of producing a DBM fibres product as claimed in any of claims 21-30 below.

The present invention can be performed in various ways, but two embodiments will now be described by way of example and with reference to the accompanying drawings, in which.

Figure 4:
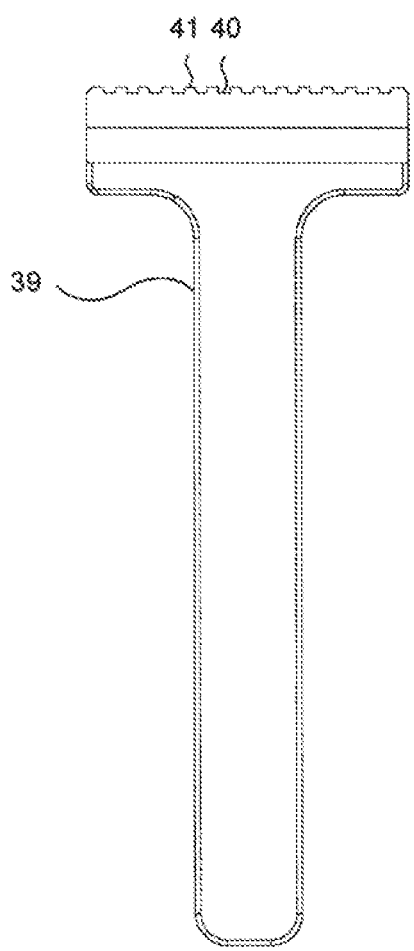
FIG. 4 is a front view of a second bone rake component of the apparatus of the first aspect of the present invention.
Figure 5:
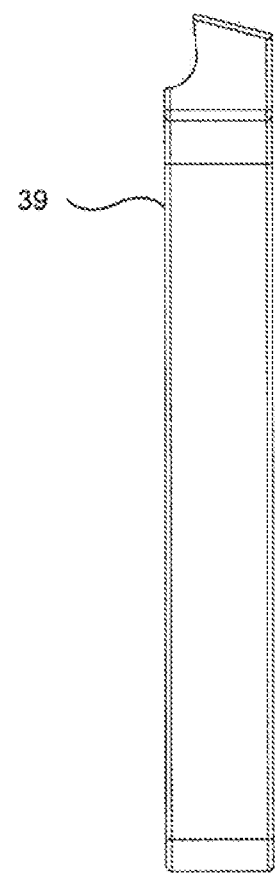
FIG. 5 is a side view of the second bone rake component of the appraratus of the first aspect of the present invention.
Figure 6:
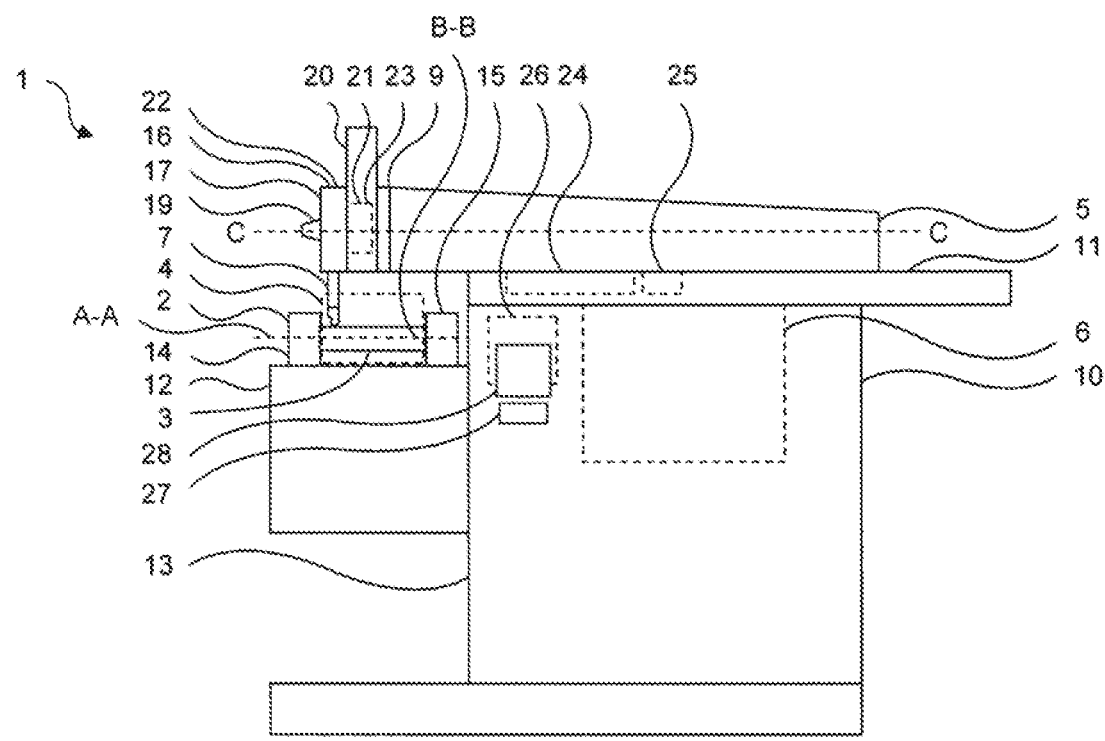
FIG. 6 is a side view of the apparatus of the first aspect of present invention with an arm component thereof in a forward position.
Figure 7:
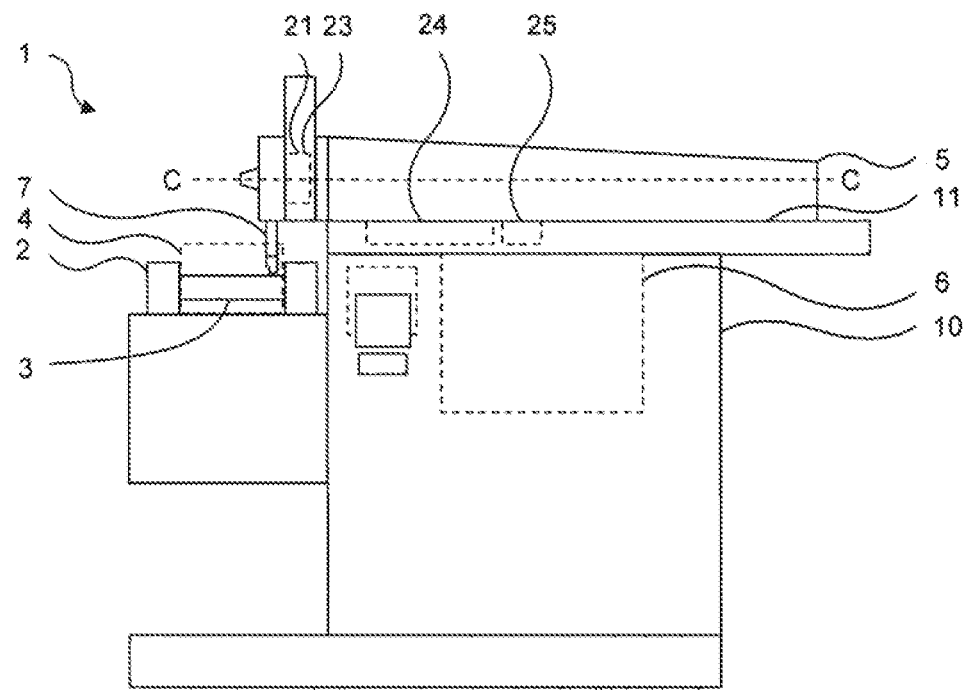
FIG. 7 is a side view of the apparatus as shown FIG. 6 with the arm component thereof in a rearward position.

As shown in FIGS. 1-9, a first apparatus for producing strips of bone fibre 1 comprises a vice 2 for securing a section of rigid bone 3 with which the apparatus 1 is used, the vice 2 defining a containment area 4 and having a compression axis A-A with which a longitudinal axis B-B of said bone 3 is substantially aligned in use. An arm 5 for reciprocal linear movement along a movement axis C-C between a rearward position, as shown in FIG. 7 and a forward position, as shown in FIG. 6. As is clear from the Figures the movement axis C-C is parallel with the compression axis A-A and is spaced therefrom in a lateral plane. A first drive mechanism, which is internal to the apparatus 1 and is illustrated with hashed outline 6, is provided for moving the arm 5 along the movement axis C-C in a reciprocal manner. A cutting head 7 comprising a first row of cutting teeth 8 is provided, which cutting head 7 is mounted to a first end 9 of the arm 5 with the first row of cutting teeth 8 coincident with the containment area 4 and disecting the lateral plane.

The apparatus 1 is a metal shaping machine of a known type which has been modified to perform the functions of the apparatus of the first aspect of the present invention. In particular, it comprises a main body 10 which supports the arm 5 for reciprocal movement on a track 11 The first drive mechanism 6 is a mechanical mechanism for moving the arm 5 back and forth on the track 11. The main body 10 also supports a plate 12 at a first side 13 thereof, on which is disposed the vice 2. The vice 2 comprises a pair of ends 14 and 15 which can be wound towards and away from each other on the plate 12 in the known way, along the compression axis A-A.

The cutting head 7 is removably mounted to the first end 9 of the arm 5 in a first adjustment mechanism 16, which comprises a mounting 17 in which a stem 18 with which the cutting head 7 is formed is releasably mounted by means of a screw 19, and a backplate 20. The mounting 17 is movable automatically up and down in relation to a back plate 20, which allows for the cutting head 7 to be moved between an upper position and a lower position in the lateral plane. This movement is facilitated by a second drive mechanism, which is internal to the apparatus 1 and is illustrated with hashed outline 21. The second drive mechanism 21 is a mechanical mechanism comprising an electrical motor for moving the mounting 17 up and down on the backplate 20. The second drive mechanism 21 can drive the first adjustment mechanism to adjust the location of the cutting head 7 in the lateral plane by increments of 0.1 mm, such that the resulting strips of bone fibre comprise such thicknesses.

As explained her below, the first adjustment mechanism 16 can adjust the location of the cutting head 7 in the lateral plane between each reciprocal movement of the arm 5 along the movement axis C-C, such that the thickness of a continuous sequence of strips of bone fibre cut from the bone 3 are substantially consistent.

Figure 8:
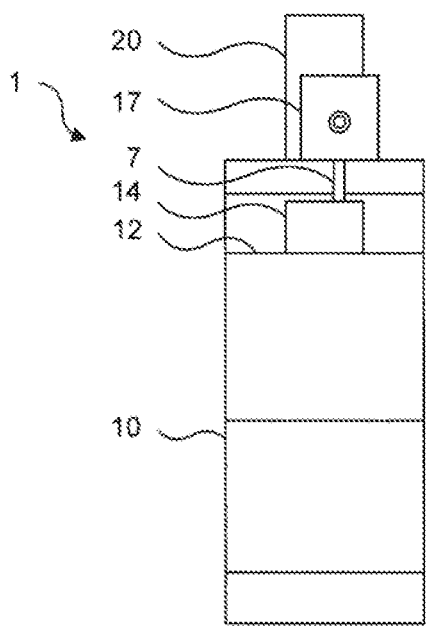
FIG. 8 is a front view of the apparatus as shown in FIG. 7 with a second adjustment mechanism component thereof in a left position.
Figure 9:
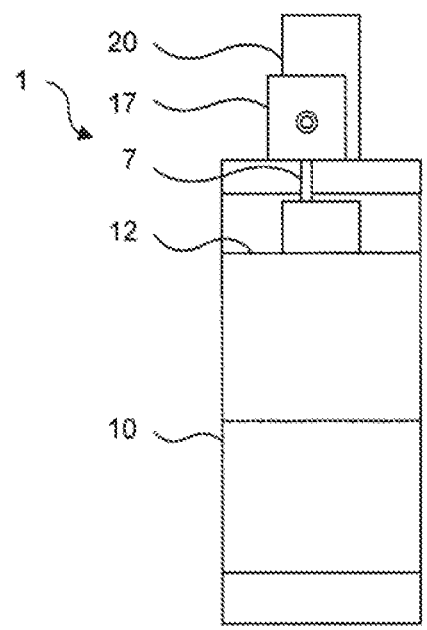
FIG. 9 is a front view of the apparatus as shown in FIG. 7 with the second adjustment mechanism component thereof in a right position.

The apparatus 1 also comprise a second adjustment mechanism 22 for adjusting the location of the cutting head 7 in a transverse plane normal to the lateral plane between a left position, as shown in FIG. 8, and a right position, as shown in FIG. 9. The second adjustment mechanism 22 is integrally formed with the first adjustment mechanism 16, and comprises the mounting 17 and the backplate 20, with the mounting 17 being movable left and right on the backplate 20. This movement is facilitated by a third drive mechanism 23, which is integral with the second drive mechanism 21, and comprises an electrical motor for moving the mounting 17 left and right on the backplate 20. This allows the user to set the area of the bone 3 from which the strips of bone fibre are to be cut.

The apparatus 1 also comprises a third adjustment mechanism, which is internal to the apparatus 1 and is illustrated with hashed outline 24. The third adjustment mechanism 24 adjusts the location of the rearward position and the forward position of the arm 5 on the movement axis is C-C. This allows the user to set the length of the strips of bone fibre which are cut from the bone 3 in this illustrative example the third adjustment mechanism 24 comprises an adjustable linkage which adjusts the throw of a connecting rod which moves the arm 5 in the reciprocal manner. A fourth drive mechanism, which is also internal to the apparatus 1 and is illustrated with hashed outline 25, drives the third adjustment mechanism 23. The fourth drive mechanism 25 is an electrical motor which acts on the connecting rod to adjust its throw. The fourth adjustment mechanism 25 can adjust the for of the rearward position and the forward position of the arm 5 on the movement axis C-C so the relative spacing between them between 40 mm and 70 mm, such that the resulting strips of bone fibre comprise such lengths.

The first, second and third adjustement mechanisms 16, 22 and 24, and the second, third and fourth drive mechanisms 6, 21, 23 and 25 are controlled by a microprocessor, which is internal to the apparatus 1 and is illustrated with hashed outline 26. It comprises an operation key pad 27 and screen 28, allowing the user to set the various parameters described above Such systems are widely known and the skilled person would be able to implement the above described features by reference to their common general knowledge in the field. Therefore, the microprocessor 26, and the manner in which it controls the first, second and third adjustement mechanisms 16, 22 and 24, and the first, second, third and fourth drive mechanisms 6, 21, 23 and 25 is not described herein in any greater depth.

Figure 1:
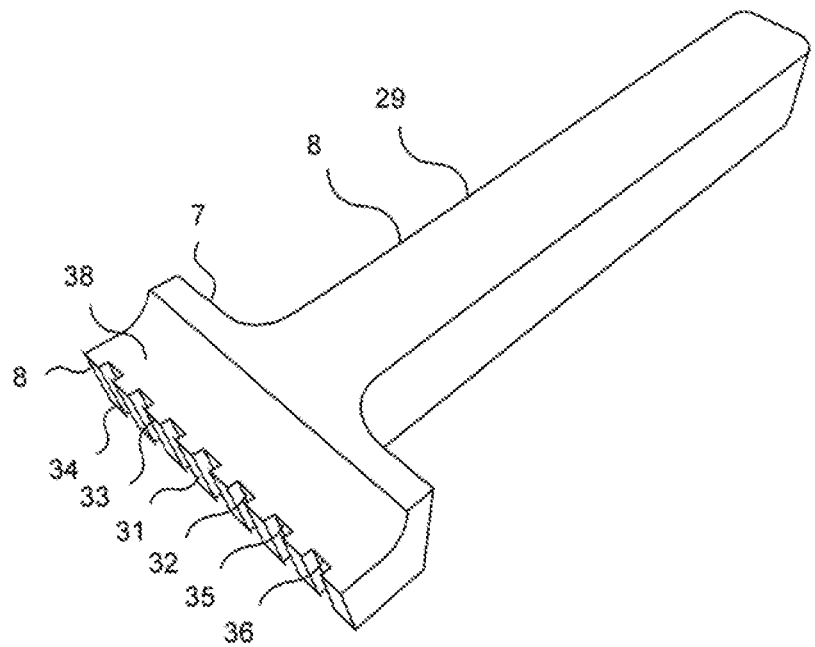
FIG. 1 is a perspective view of a bone rake component of a the apparatus of the first aspect of the present invention.
Figure 2:
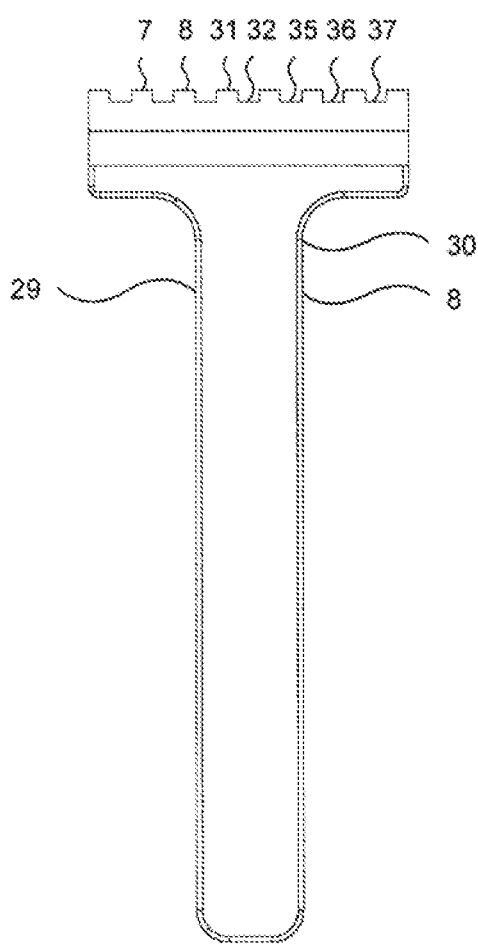
FIG. 2 is a front view of a first bone rake component of the apparatus of the first aspect of the present invention.
Figure 3:
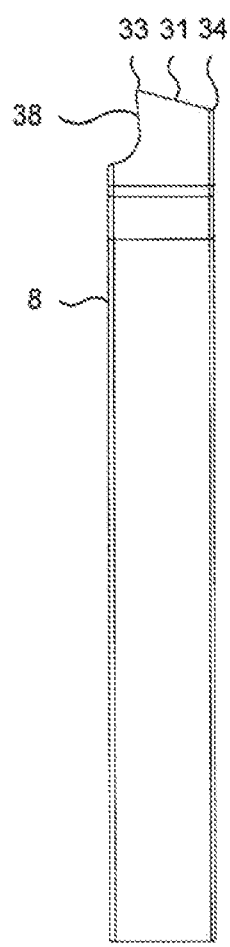
FIG. 3 is a side of the first bone rake component of the appraratus of the first aspect of the present invention.

FIGS. 1-3 show the cutting head 7 in greater detail. It comprises a bone rake 29 comprising the elongate stem 8 with the cutting head 7 formed at a first end 30 thereof. The cutting head 7 comprises a lower end face 31 with a plurality of parallel troughs 32 formed therein, and the first row of cutting teeth 8 comprise remaining portions of a leading edge 33 of the lower end face 31 between the troughs 32. As such the cutting head 7 has a crenelated shape in which the cutting teeth 8 are at the top of each of the battlements thereof. The width of each trough 32 is the same as the width of each tooth of the first row of teeth 8.

The troughs 32 extend from the leading edge 33 to a trailing edge 34 of the lower end face 31. As is clear from FIG. 3, the lower end face 31 is angled in relation to the stem 8, and this is such that when in situ in the apparatus 1 the lower end face 31 is arranged at an angle of 15 degrees to the compression axis C-C, and the trailing edge 34 is spaced from the compression axis C-C a greater distance than the leading edge 31. With this construction there is space under the lower end face 31 behind the first row of cutting teeth 8 which prevents the lower end face 31 from binding with the surface of the bone 3. This is particularly the case when the first row of cutting teeth 8 descend into the bone 3 after a number of cuts have been made.

The cutting head 7 comprises a second row of cutting teeth 35 comprising leading edges 38 of inner ends 37 of the plurality of parallel troughs 32. As such, the second row of cutting teeth 35 is formed by the bases of the battlements of the crenelated shape of the cutting head 7. With this formation the first row of cutting teeth 8 initiate the cutting of the bone 3, and the second row of cutting teeth 35 begin to cut the bone 3 when the depth of the cuts formed by the first row of cutting teeth 8 equal the depth of the troughs 32. From that point, both the first row of cutting teeth 8 and the second row of cutting teeth 35 will both cut strips of bone fibre from the bone 3. This construction allows for the maximum number of strips of bone fibre to be cut from the bone 3. Each strip will be the same width because the troughs 32 are the same width as each tooth of the first row of teeth 8.

As is also clear from FIG. 3, the cutting head 7 comprises a front face 38 which is at an angle to the stem 8, and this is such that when in situ in the apparatus 1 the front face 38 is at an angle to the transverse plane normal to the lateral plane such that said second row of cutting teeth 35 is rearward of said first row of cutting teeth 8. This shape occurs because the first row of cutting teeth 8 need to be arranged at an angle to the bone 3 in order to cut it. The first row of cutting teeth 8 comprises a cutting angle of 5 degrees to the transvese plane. The second row of cutting teeth 35 comprises the same cutting angle. With this arrangement the cutting teeth 8 and 35 are applied to the surface of the bone 3 at an angle of substantially 95 degrees (as the transverse plane is normal thereto). This angle has been chosen because it produces thin slices of bone fibre while at the same time preventing the teeth 8 and 35 from being chipped away by the force applied by the first drive mechanism 6.

The row of cutting teeth 8 and the troughs 32 comprise widths of 2 mm. As such, the width of the strips of bone fibre cut from the bone 3 by the first row of cutting teeth 8 and the second row of cutting teeth 35 have the same width.

The apparatus 1 is used to procude strips of bone fibre as follows. Firstly a prepared section of bone 3 is secured in the vice 2, with its longitudinal axis B-B aligned with the compression axis A-A. The section of bone 3 is taken from a long bone such as a femur, tibia or humerus, and is first cut to remove both ends in order to create a middle shaft. All the surrounding tissues such as muscle and periosteal membrane are removed mechanically or by hand, using blunt instruments such as a scalpel blade, periosteal elevator or osteotome. The debrided shaft is then washed and cleaned to remove bone marrow from the medullary canal.

The bone rake 29 is then placed in the mounting 17 and secured therein by the screw 18. Using the keypad 27 and screen 28 the user then programmes the microprocessor 26 to cut desired sizes of strips of bone fibre from the bone 3. In particular, the third adjustment mechanism 24 is accessed to determine the length of the strips, which length can be chosen based on the length of the bone 3. The fourth drvie mechanism 25 then adjusts the apparatus 1 so the arm 5 will move reciprocally back and forth on the track 11 by the chosen distance. The first adjustment mechanism 16 is accessed to determine the thickness of the strips to be cut, which can be chosen from a thickness of between 0.1 mm to 0.4 mm. The second drive mechanism 21 then lowers the mounting 17 until the bone rake 29 contacts the bone 3, and sufficient force is applied that when the arm 5 is moved for the first time strips of the desired thickness are shaved therefrom by the first row of cutting teeth 8.

The second adjustment mechanism a 22 can optionally be accessed to adjust the position of the bone rake 29 in the transverse plane. The user may choose to adjust the position of the bone rake 29 to any position between the left position as shown in FIG. 8, and the right position as shown in FIG. 9. The third drive mechanism 23 moves the mounting 17 accordingly.

Once the bone rake 29 is in the desired position the first drive mechanism 6 moves the arm 5 from the rearward position as shown in FIG. 7 to the forward position as shown in FIG. 6. When it does this the cutting head 7 moves over the bone 3 and the first row of teeth 8 cut strips of bone fibre therefrom. The cut strips of bone fibre are driven up against the front face 38, and tend to form curved shapes, and then fall onto the plate 12, or are otherwise collected. The arm 5 only moves as far as it is permitted by the third adjustment mechanism 24, which has been set by the user.

The first drive mechanism 6 then returns the arm 5 from the forward position shown in FIG. 6 to the rearward position shown in FIG. 7. The first adjustment mechanism 16 then adjusts the location of the cutting head 7 in the lateral plane by lowering the mounting 17 relation to the backplate 20 by the distance set by the user of between 0.1 mm and 0.4 mm. Once again sufficient force is applied that when the arm 5 is moved once again further strips of bone fibre of the desired thickness are cut from the bone 3.

This sequence of movements is repeated in order to generate a continuous sequence of cut strips of bone fibre.

Eventually, after a number of reciprocal movements of the arm 5, the first row of teeth 8 will have cut a row of parallel indentations into the bone 3. When the depth of these indentations equals the depth of the troughs 32, the second row of cutting teeth 35 will begin to cut strips of bone fibre from the bone 3. Each strip will be the same width because the troughs 32 are the same width as each tooth of the first row of teeth 8. These cut strips of bone fibre are also driven up against the front face 38 and fall onto the plate 12, or are otherwise collected. As such, all the surface of the bone 3 underneath the cutting head 7 is processed into cut strips bone fibre.

The reciprocal movement of the arm 5 is continued until all the bone 3 has been processed.

In the event that the bone 3 is wider than the cutting head 7, the user can stop the operation of the apparatus 1, and use the keypad 27 and screen 28 to employ the second adjustment mechanism 22 to adjust the position of the cutting head 7 in the transverse plane. This allows for unprocessed parts of the bone 3 on either side of the location of a preceding sequence of cuts to then be processed.

At any time user can stop the operation of the apparatus 1 and adjust the position of the bone 3. They may do this in order to rotate it on its longitudinal axis B-B in order to allow for unprocessed parts of the bone 3 to then be processed.

FIGS. 4 and 5 show an alternative sec end bone rake 39, which is the same as bone rake 29, except that the troughs 40 and the teeth of the first row of cutting teeth 41 are 1 mm wide, such that 1 mm wide strips of bone fibre are cut from the bone. Therefore, the user can select either the bone rake 29 or the bone rake 39 to adjust the width of the cut strips of bone fibre. This provides support for the kit of parts of the second aspect of the present invention.

Figure 10:
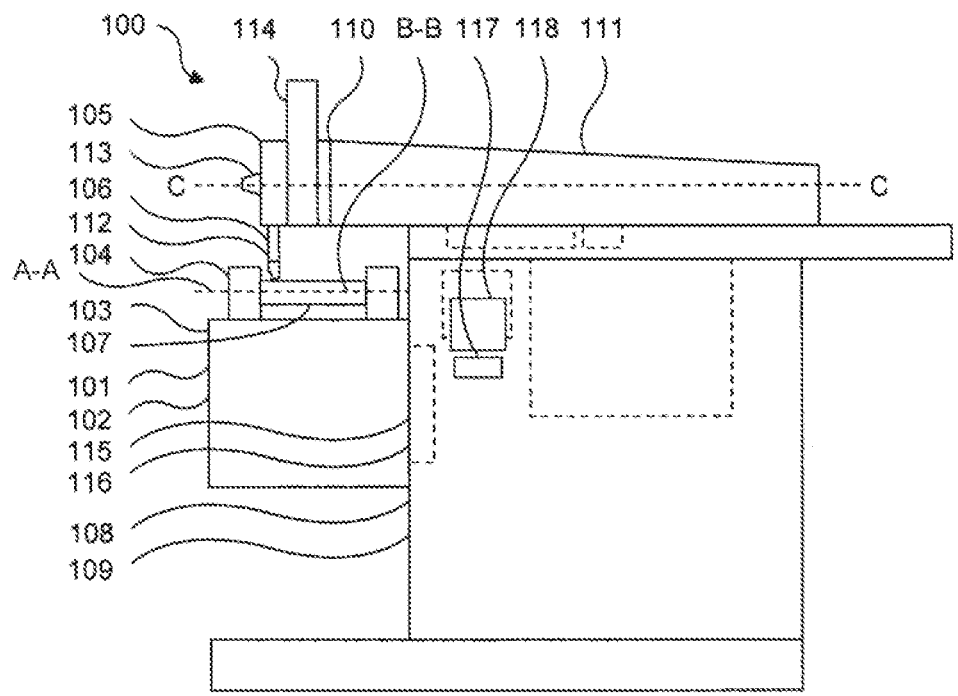
FIG. 10 is a side view of the second apparatus according to the first aspect of the present invention in a forward position.
Figure 11:
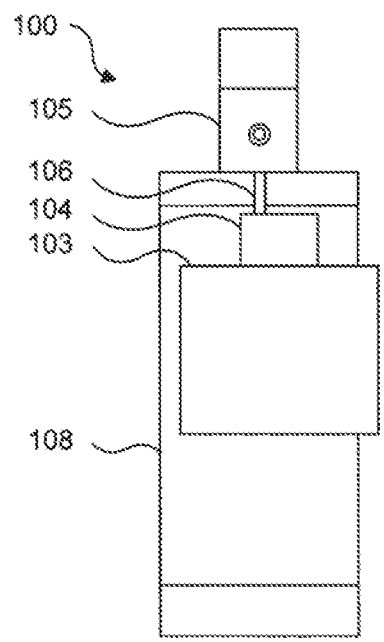
FIG. 11 is a front view of the apparatus as shown in FIG. 10 with a second mechanism component thereof in a left position.
Figure 12:
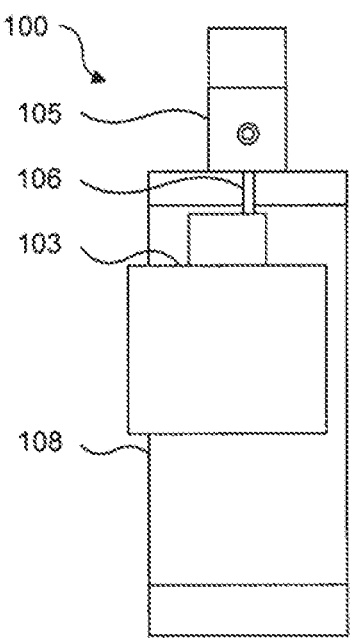
FIG. 12 is a front view of the apparatus as shown in FIG. 10 with the second adjustment mechanism component thereof in a right position.

FIGS. 10 to 12 show an alternative embodiment in which apparatus 100 is similar to apparatus 1 described above, but in which the first adjustment mechanism 101 and the second adjustment mechanism 102 move the plate 103, and therefore the vice 104, instead of the mounting 105. This achives the same relative movment as described above between the cutting head 106 and the bone 107 to achieve the same ends, but it may be a preferred arrangement.

In particular, the main body 108 supports the plate 103 at a first side 109 thereof, on which is disposed the vice 104. The cutting head 106 is removably mounted to the first end 110 of the arm 111 in the mounting 105, in which a stem 112 with which the cutting head 106 is formed is releasably mounted by means of a screw 113, and a backplate 114.

The plate 103 is movable up and down in relation to main body 108, which allows for the vice 104 to be moved between an upper position and a lower position in the lateral plane. This movement is facilitated by a second drive mechanism, which is internal to the apparatus 100 and is illustrated with hashed outline 115. The second drive mechanism 115 is a mechanical mechanism comprising an electrical motor for moving the plate 103 up and down relative to the main body 108. The second drive mechanism 115 can drive the first adjustment mechanism 101 to adjust the location of the vice 104 in the lateral plane by increments of 0.1 mm, such that the resulting strips of bone fibre comprise such thicknesses.

The first adjustment mechanism 101 can adjust the location of the vice 104 in the lateral plane between each reciprocal movement of the arm 111 along the movement axis C-C, such that the thickness of a continuous sequence of strips of bone fibre cut from the bone 107 are substantially consistant.

The apparatus 100 also comprises the second adjustment mechanism 102 for adjusting the location of the vice 104 in a transverse plane normal to the lateral plane between a left position, as shown in FIG. 11, and a right position, as shown in FIG. 12. The second adjustment mechanism 102 is integrally formed with the first adjustment mechanism 101, and the movement it provides is facilitated by a third drive mechanism 116, which is integral with the second drive mechanism 115, and comprises an electrical motor for moving the plate 103 left and right relative to the main body 108. This allows the user to set the area of the bone 3 from which the strips of bone fibre are to be cut.

In all other respects the apparatus 100 is the same as apparatus 1 described above, and operates in the same ways.

The apparatus 1 and 100 described above can be altered without departing from the scope of claim 1. For example, in an alternative emobodiment (not shown) the first, second and third adjustment mechanisms are all manually operated by the user rather than being automated. This is less efficient, but it make the apparatus more economic.

Figure 13:
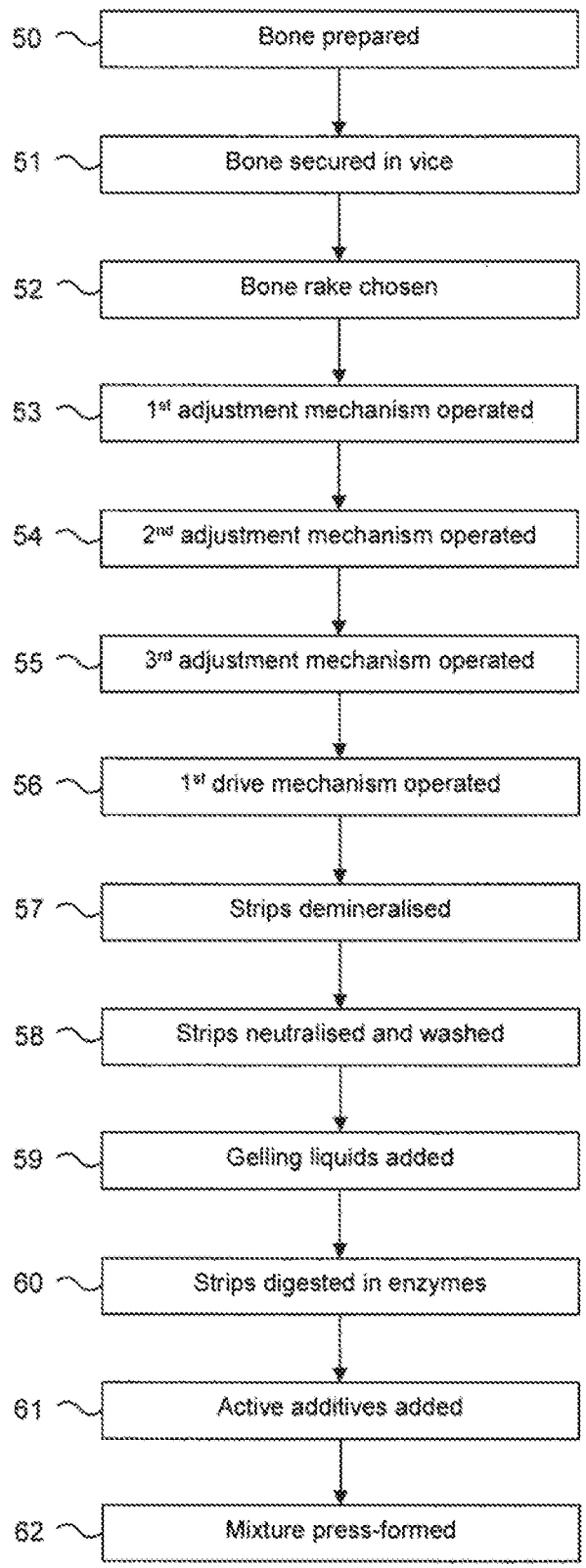
FIG. 13 is view of a method of the third aspect of the present invention.

As explained above, the invention also includes a method of producing strips of bone fibre which using apparatus 1 or apparatus 100. The steps of such a method of using apparatus 1 are illustrated in FIG. 13. As shown therein, in the first step 50 the bone is prepared for cutting. The bone is taken from a long bone such as a femur, tibia or humerus, and is first cut to remove both ends in order to create a middle shaft. All the surrounding tissues such as muscle and periosteal membrane are removed mechanically or by hand, using blunt instruments such as a scalpel blade, periosteal elevator or osteotome. The debrided shaft is then washed and cleaned to remove bone marrow from the medullary canal.

In a second step 51 the bone is secured in the vice 2, with a longitudinal axis B-B thereof substantially aligned with the compression axis A-A.

In the third to sixth steps 52-55 the user sets up the apparatus as desired. In particular, in the third step 52 they chose from bone rakes 29 and 39 to set the width of the strips of bone fibre.

In the fourth step 53 the user uses the keypad 27 and screen 28 to programme the microprocessor 26 to operate the first adjustment mechanism 16 to adjust the location of the cutting head 7 in the lateral plane initially, and the between each reciprocal movement of the arm 5, to achive a desired thickness of the strips of bone fibre.

In the fifth step 54 the user optionally uses the keypad 27 and screen 28 to programme the microprocessor 26 to operate the second adjustment mechanism 22 to adjust the location of the cutting head 7 in the transverse plane between the left position and the right position, to set the area of the bone 3 from which the strips of bone fibre are cut.

In the sixth step 55 the user optionally uses the keypad 27 and screen 28 to programme the microprocessor 26 to operate the third adjustment mechanism 24 to set the location of a rearward position and a forward position of the arm 5, in order to set the length of strips of bone figure which are cut.

In a seventh step 56 the first drive mechanism operated to move the arm 5 of the apparatus 1 along the movement axis C-C in a reciprocal manner to generate the strips of bone fibre.

In the eigth to thirteenth steps a DBM fibres product is formulated comprising the cut strips of bone fibre produced in steps one to seven.

In the eigth step 57 the cut strips of bone fibre are demineralised by immersing them in hydrochloric acid of between 0.5 M to 0.6 M until the cut strips of bone fibre are within the range of between substantially 1% and substantially 4% w/w of residual calcium content.

In the ninth step 58 the demineralised cut strips of bone fibre are neutralised in a buffer solution and washed thoroughly in water.

In the tenth step 59 the demineralised cut strips of bone fibre are mixed with one or more gelling liquids, chosen from glycerol, gelatin and/or cellulose to form a surgical mixture.

In the eleventh step 60 the demineralised cut strips of bone fibre are digested in enzymes such as trypsin or some mild acids to make injectable bone gel.

In the twelfth step 61 the demineralised cut strips of bone fibre are mixed with one or more pharmaceutically active additivies chosen from antibiotics, calcium phosphate based materials, stem cells and or growth factors.

In the thirteenth step 62 the surgical mixture is press-formed into a predetermined shape chosen from a ball, a boat, a pellet, a cylinder or a cone.

Each of the tenth to thirteenth to thirteenth steps is optional, and is used as and when desired to procude different kinds of DBM products.

The apparatus 100 described above can also used to perform a very similar method. The only differences are: a) in the fourth step 53 the user uses the keypad 117 and screen 118 to programme the microprocessor 119 to operate the first adjustment mechanism 101 to adjust the location of the vice 104 in the lateral plane initially, and the between each reciprocal movement of the arm 111, to achive a desired thickness of the strips of bone fibre; and b) in the fifth step 54 the user optionally uses the keypad 117 and screen 118 to programme the microprocessor 119 to operate the second adjustment mechanism 102 to adjust the location of the vice 104 in the transverse plane between the left position and the right position, to set the area of the bone 3 from which the strips of bone fibre are cut.

According to the fourth aspect of the present invention there is provided a DBM fibres product produced using the method of producing a fibres product as claimed in any of claims 21-30 below. The above described method as illustrated in FIG. 13 provides support for the fourth aspect of the present invention.

Therefore, the sent invention provides apparatus which employs a linear relative movement between the section of bone and the cutting head in order to shave strips of bone fibre therefrom. The invention also provices multiple ways to adjust the apparatus to set the width, depth and length of the strips. The invention also provides a new and efficient cutting head with two rows of cutting teeth and an efficient cutting action. Furthermore, the invention provides a kit of parts, a method of producing a DBM product, and a DBM product itself, all of which feature the same inventive features as the first aspect of the present invention.

The invention claimed is:

1. The apparatus for producing strips of bone fibre comprising:
   a vice for securing a section of rigid bone with which said apparatus is used, said vice defining a containment area and having a compression axis with which a longitudinal axis of said bone is substantially aligned in use,
   an arm for reciprocal linear movement along a movement axis between a rearward position and a forward position, said movement axis being parallel with said compression axis and spaced therefrom in a lateral plane,
   a first drive mechanism for moving said arm along said movement axis in a reciprocal manner, and
   a cutting head comprising a first row of cutting teeth, which cutting head is mounted to a first end of said arm with said first row of cutting teeth coincident with said containment area and dissecting said lateral plane.

2. The apparatus as claimed in claim 1 in which said apparatus comprises a first adjustment mechanism for adjusting the location of said cutting head in said lateral plane between an upper position and a lower position.

3. The apparatus as claimed in claim 2 in which said apparatus comprises a second drive mechanism for driving said first adjustment mechanism.

4. The apparatus as claimed in claim 2 in which said apparatus comprises a bone rake comprising an elongate stem with said cutting head formed at a first end thereof, which bone rake is removably mountable in said first adjustment mechanism with said elongate stem aligned with said lateral plane.

5. The apparatus as claimed in claim 1 in which said apparatus comprises a first adjustment mechanism for adjusting the location of said vice in said lateral plane between an upper position and a lower position.

6. The apparatus as claimed in claim 5 in which said apparatus comprises a bone rake comprising an elongate stem with said cutting head formed at a first end thereof, which bone rake is removably mountable on said apparatus with said elongate stem aligned with said lateral plane.

7. The apparatus as claimed in claim 1 in which said apparatus comprises a second adjustment mechanism for adjusting the location of said cutting head in a transverse plane normal to said lateral plane between a left position and a right position.

8. The apparatus as claimed in claim 7 in which said apparatus comprises a third drive mechanism for driving said second adjustment mechanism.

9. The apparatus as claimed in claim 1 in which said apparatus comprises a second adjustment mechanism for adjusting the location of said vice in a transverse plane normal to said lateral plane between a left position and a right position.

10. The apparatus as claimed in claim 9 in which said apparatus comprises a fourth drive mechanism for driving said third adjustment mechanism.

11. The apparatus as claimed in claim 1 in which said apparatus comprises a third adjustment mechanism for adjusting the location of said rearward position and said forward position of said arm on said movement axis.

12. The apparatus as claimed in claim 1 in which said cutting head comprises a lower end face, in which said lower end face comprises a plurality of parallel troughs formed therein, and in which said first row of cutting teeth comprises remaining portions of a leading edge of said lower end face between said troughs.

13. The apparatus as claimed in claim 12 in which said plurality of parallel troughs extend from said leading edge to a trailing edge of said lower end face.

14. The apparatus as claimed in claim 13 in which said lower end face is at an angle of substantially 15 degrees to said compression axis, and in which said trailing edge is spaced from said compression axis a greater distance than said leading edge.

15. The apparatus as claimed in claim 12 in which said apparatus comprises a second row of cutting teeth comprising leading edges of inner ends of said plurality of parallel troughs.

16. The apparatus as claimed in claim 15 in which said cutting head comprises a front face which is at an angle to a transverse plane normal to said lateral plane, such that said second row of cutting teeth is rearward of said first row of cutting teeth.

17. The apparatus as claimed in claim 15 in which said second row of cutting teeth comprises a cutting angle of substantially 5 degrees to said transverse plane.

18. The apparatus as claimed in claim 1 in which said first row of cutting teeth comprises a cutting angle of substantially 5 degrees to a transverse plane normal to said lateral plane.

19. The apparatus as claimed in claim 1 in which the width of each tooth of the first row of cutting teeth is between substantially 1 mm and substantially 2 mm.

20. A method of producing a DBM fibres product using apparatus as claimed claim 1, comprising the steps:
   (i) securing a section of rigid bone in a vice of said apparatus with a longitudinal axis thereof substantially aligned with a compression axis of said vice;
   (ii) operating a first drive mechanism of said apparatus to move an arm of said apparatus along a movement axis thereof in a reciprocal manner, such that a first row of cutting teeth of a cutting head of said apparatus cuts strips of bone fibre from said section of rigid bone; and
   (iii) formulating a DBM fibres product comprising the cut strips of bone fibre.

21. A method of producing a DBM fibres product as claimed in claim 20 including the additional step of operating a first adjustment mechanism of said apparatus to adjust the location of said cutting head or said vice in a lateral plane between an upper position and a lower position to set the thickness of strips of bone fibre cut from said section of rigid bone.

22. A method of producing a DBM fibres product as claimed in claim 21 including the additional step of operating said first adjustment mechanism to adjust the location of said cutting head or said vice in said lateral plane, between each reciprocal movement of said arm along said movement axis, such that the thickness of a continuous sequence of strips of bone fibre cut from said section of rigid bone are substantially consistent.

23. A method of producing a DBM fibres product as claimed in claim 20 including the additional step of operating a second adjustment mechanism of said apparatus to adjust the location of said cutting head or said vice in a transverse plane between a left position and a right position, to set the area of the section of rigid bone from which said strips of bone fibre are cut.

24. A method of producing a DBM fibres product as claimed in claim 20 including the additional step of operating a third adjustment mechanism of said apparatus to adjust the location of a rearward position and a forward position of said arm on said movement axis to set the length of strips of bone fibre cut from said section of rigid bone.

25. A method of producing a DBM fibres product as claimed in claim 20 including the additional step of demineralising said cut strips of bone fibre by immersing them in hydrochloric acid of between 0.5M to 0.6M until said cut strips of bone fibre are within the range of between substantially 1% and substantially 4% w/w of residual calcium content.

26. A method of producing a DBM fibres product as claimed in claim 25 including the additional step of mixing the demineralised cut strips of bone fibre with one or more gelling liquids, chosen from glycerol, gelatin and/or cellulose to form a surgical mixture.

27. A method of producing a DBM fibres product as claimed in claim 26 including the additional step of press-forming the surgical mixture into a predetermined shape chosen from a ball, a boat, a pellet, a cylinder or a cone.

28. A method of producing a DBM fibres product as claimed in claim 25 including the additional step of digesting the demineralised cut strips of bone fibre in enzymes and/or mild acids to make injectable bone gel.

29. A method of producing a DBM fibres product as claimed in claim 25 including the additional step of mixing the demineralised cut strips of bone fibre with one or more pharmaceutically active additives chosen from antibiotics, calcium phosphate based materials, stem cells and or growth factors.

30. A DBM fibres product produced using the method of producing a DBM fibres product as claimed in claim 20.

31. A kit of parts comprising:
  apparatus for producing strips of bone fibre comprising a vice for securing a section of rigid bone with which said apparatus is used, said vice defining a containment area and having a compression axis with which a longitudinal axis of said bone is substantially aligned in use, an arm for reciprocal linear movement along a movement axis between a rearward position and a forward position, said movement axis being parallel with said compression axis and spaced therefrom in a lateral plane, a first drive mechanism for moving said arm along said movement axis in a reciprocal manner, and a first cutting head comprising a first row of cutting teeth, which first cutting head is removably mountable to a first end of said arm with said first row of cutting teeth coincident with said containment area and dissecting said lateral plane; and
  one or more further cutting heads each comprising a first row of cutting teeth with teeth of a different width to teeth of said first cutting head, each of which one or more further cutting heads is removably mountable to a first end of said arm with said first row of cutting teeth coincident with said containment area and dissecting said lateral plane.

* * * * *